United States Patent [19]

Kawamura et al.

[11] Patent Number: 5,516,431
[45] Date of Patent: *May 14, 1996

[54] METHOD OF WASHING SECONDARY FILTER IN PROCESS FOR FILTERING PLASMA

[75] Inventors: Akio Kawamura; Motoki Yonekawa, both of Sapporo; Osamu Kaneko, Naruto; Hiroshi Kamogawa, Tokushima, all of Japan

[73] Assignee: Otsuka Pharmaceutical Factory, Inc., Naruto, Japan

[*] Notice: The portion of the term of this patent shall not extend beyond the expiration date of Pat. No. 5,314,624.

[21] Appl. No.: 302,774

[22] PCT Filed: Jan. 21, 1994

[86] PCT No.: PCT/JP94/00085

§ 371 Date: Sep. 19, 1994

§ 102(e) Date: Sep. 19, 1994

[87] PCT Pub. No.: WO94/16751

PCT Pub. Date: Aug. 4, 1905

[30] Foreign Application Priority Data

Jan. 28, 1993 [JP] Japan .................. 5-012302

[51] Int. Cl.$^6$ .......................... B01D 11/00; B01D 61/00; C02F 1/44
[52] U.S. Cl. .......................... 210/645; 210/650; 210/741; 210/791; 210/798; 210/805; 604/5; 604/6
[58] Field of Search .................. 210/645, 650, 210/741, 791, 798, 805, 90, 321.64, 321.68; 604/5, 6

[56] References Cited

U.S. PATENT DOCUMENTS

| | | | |
|---|---|---|---|
| 4,919,817 | 4/1990 | Schoendorfa et al. | 210/639 |
| 4,936,980 | 6/1990 | Yoshimichi et al. | 210/647 |
| 5,186,835 | 2/1993 | Masuoka et al. | 210/500.36 |
| 5,242,384 | 9/1993 | Robinson et al. | 604/4 |
| 5,261,876 | 11/1993 | Popovich et al. | 604/28 |
| 5,298,016 | 3/1994 | Gordon | 604/4 |
| 5,314,624 | 5/1994 | Kawakura et al. | 210/645 |

FOREIGN PATENT DOCUMENTS

| | | |
|---|---|---|
| 531540 | 3/1993 | European Pat. Off. . |
| 59-11865 | 1/1984 | Japan . |
| 60-198158 | 10/1985 | Japan . |

OTHER PUBLICATIONS

International Search Report Appln. No. PCT/JP94/00085, dated Mar. 18, 1994.

*Primary Examiner*—N. Bhat
*Attorney, Agent, or Firm*—Armstrong, Westerman, Hattori, McLeland & Naughton

[57] ABSTRACT

In a plasma filtration process including a treatment with a primary filter for separating blood into blood cells and plasma and a treatment with a secondary filter for removing harmful macromolecules from the separated plasma for purification, the secondary filter is washed by passing a washing liquid through an inner chamber of the filter, an outer chamber thereof or both the chambers in an amount corresponding to 5 to 50% of the priming volume of the filter every time the filtration pressure has reached 70 to 100% of the withstanding pressure of the secondary filter. This washing procedure reduces the time required for the filtration of plasma to about 60 to 70% of the time conventionally needed, shortens the patient restraining time, and decreases the amount of washing liquid to be used to consequently diminish the disposal loss of plasma from the system.

7 Claims, 3 Drawing Sheets

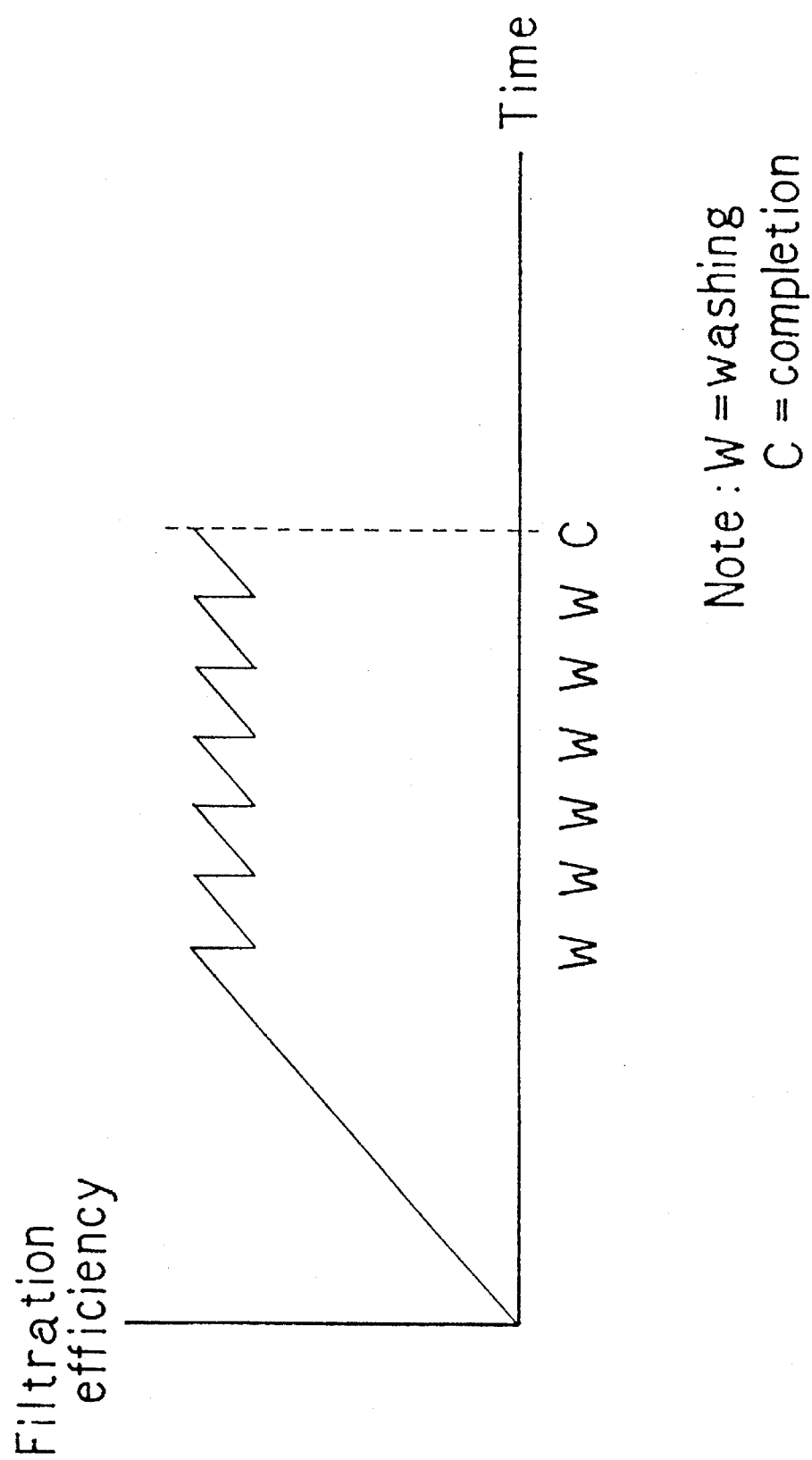

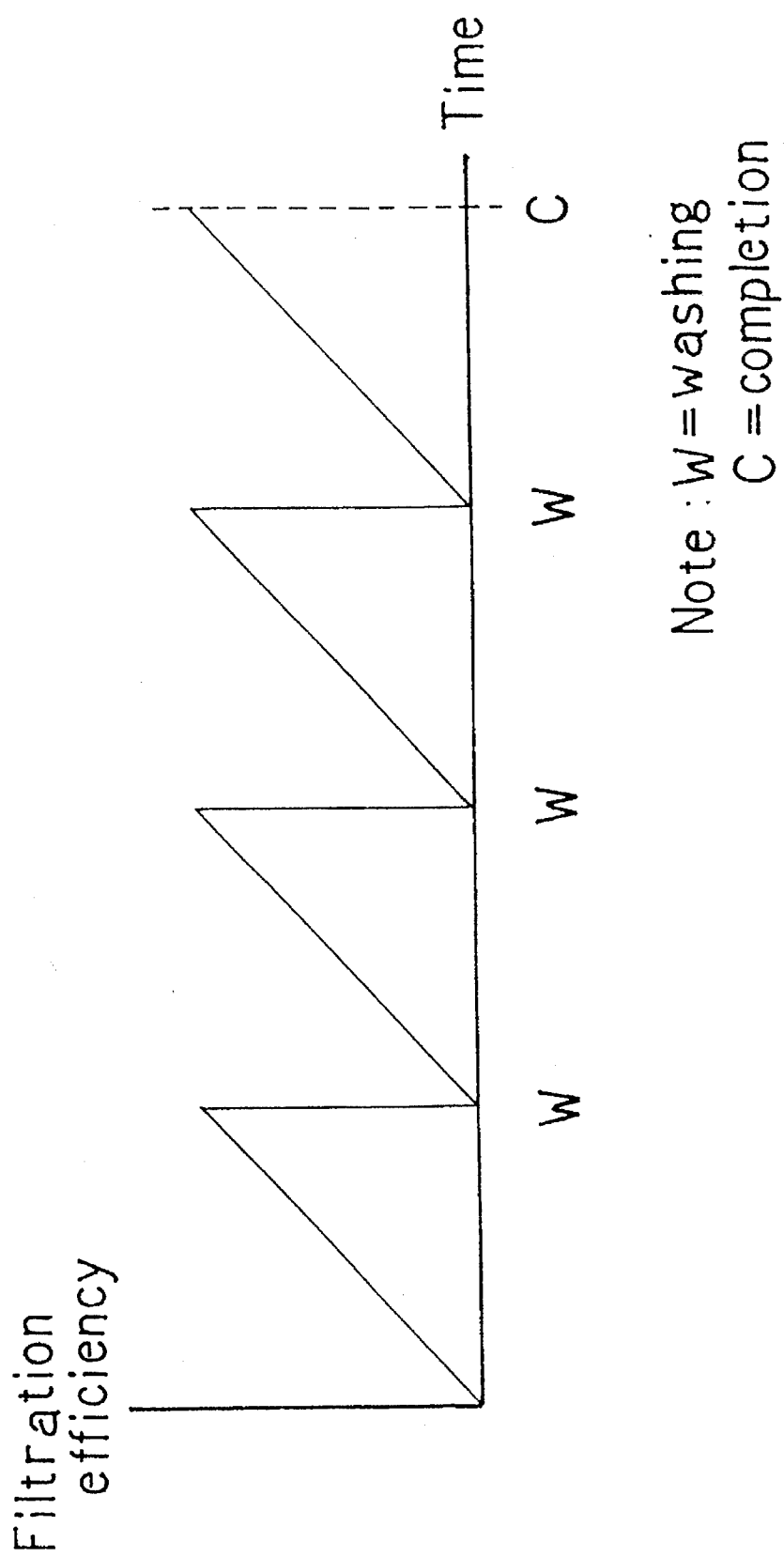

METHOD OF WASHING SECONDARY FILTER IN PROCESS FOR FILTERING PLASMA

TECHNICAL FIELD

The present invention relates to a method of washing a secondary filter in a process for filtering plasma.

BACKGROUND ART

The plasma filtration processes include so-called double filtration plasmapheresis by which the substance to be removed is selected according to the pore size of a secondary filter, and so-called cryofiltration for removing pathogenic substances from plasma by a secondary filter with cooling. In either of these processes, continued filtration of plasma tends to gradually clog the secondary filter, so that it is necessary to eliminate clogging in the course of filtration.

There are two methods of eliminating clogging; one is replacement of the secondary filter by another one, and the other is washing the secondary filter with physiological saline or the like. The latter is used generally since the secondary filter is expensive.

As a method of washing the secondary filter, it is already proposed to wash the filter with a wash liquor in an amount approximately equal to the priming volume of the filter to ten-odd times the volume when the filtration pressure has reached 60% of the withstanding pressure of the secondary filter (maximum pressure to withstand the filtration pressure with safety), for example, 300 mm Hg (e.g., Tetsuzo Agishi et al., "Double Filtration Plasmapheresis," published by Igaku Shoin). However, the conventional washing method which consumes a large amount of wash liquor approximately equal to the priming volume to ten-odd times the volume gives rise to the problem of resulting in a greatly reduced filtration efficiency to necessitate much time for removing the pathogenic substance from plasma because every time the secondary filter is washed, the interior of the filter is entirely replaced by the wash liquor with the cake almost completely washed away by washing. The term filtration efficiency as used herein refers to the rate of removal of the substance per unit time. For example, in the case of cryofiltration wherein usually 2 to 4 liters of plasma needs to be treated in circulation, the time taken is as long as about 4 hours in total including the time required for washing the secondary filter, and the patient must be placed under restraint during this period. It is desired to shorten the time.

DISCLOSURE OF THE INVENTION

The main object of the present invention is to provide a method of washing a secondary filter in a process for filtering plasma, the method being adapted to shorten the time required for the filtration of plasma.

Another object of the present invention is to provide a method of washing the secondary filter in the plasma filtration process with a reduced amount of wash liquor and consequently with a diminished disposal loss of plasma from the system.

Other features of the present invention will be made apparent from the following description.

In a plasma filtration process including a treatment with a primary filter for separating blood into blood cells and plasma and a treatment with a secondary filter for removing harmful macromolecules from the separated plasma for purification, the present invention provides a method of washing the secondary filter characterized in that the secondary filter is washed by passing a wash liquor through an inner chamber of the filter, an outer chamber thereof or both the chambers in an amount corresponding to 5 to 50% of the priming volume of the filter every time the filtration pressure has reached 70 to 100% of the withstanding pressure of the secondary filter.

As a preferred mode of the present invention, the secondary filter is washed by passing the wash liquor through the inner chamber of the filter, the outer chamber thereof or both the chambers in an amount corresponding to 5 to 15% of the priming volume of the filter every time the filtration pressure has reached 80 to 90% of the withstanding pressure of the secondary filter.

In the present invention, the withstanding pressure of the secondary filter means the maximum pressure at which the secondary filter is capable of withstanding the filtration pressure with safety.

Further the priming volume means the total amount of a liquid filling the inner chamber and the outer chamber of the secondary filter.

The primary filter and the secondary filter have incorporated therein thousands of hollow fibers usually made of cellulose diacetate, polyvinyl alcohol, polyethylene, polypropylene, polysulfone, EVAL, PMMA (polymethyl methacrylate), PAN (polyacrylonitrile) or the like. In pore size, the hollow fibers are usually 0.2 to 0.6μ for the primary filter 3, and usually about 0.01 to 0.1μ for the secondary filter 7. The primary and secondary filters are known and available as commercial products.

The withstanding pressure of the secondary filter corresponds to the withstanding pressure of the hollow fibers incorporated therein. The withstanding pressure, which varies depending, for example, on the material and/or the wall thickness of the fibers, is usually 500 mmHg.

The priming volume of the secondary filter is not limited specifically but is suitably determined usually from the range of about 150 to about 400 ml in view of the amount of plasma to be treated in circulation. The amount of plasma to be treated in circulation is determined suitably in accordance with the pathological state of the patient.

BRIEF DESCRIPTION OF THE DRAWINGS

FIG. 2 is a graph schematically showing the relationship of the filtration efficiency with the frequency of washing in the method of the invention and the time required for an experiment; and FIG. 3 is a graph schematically showing the relationship of the filtration efficiency with the frequency of washing in a comparative example and the time required for an experiment.

BEST MODE OF PRACTICING THE INVENTION

Figure 1:
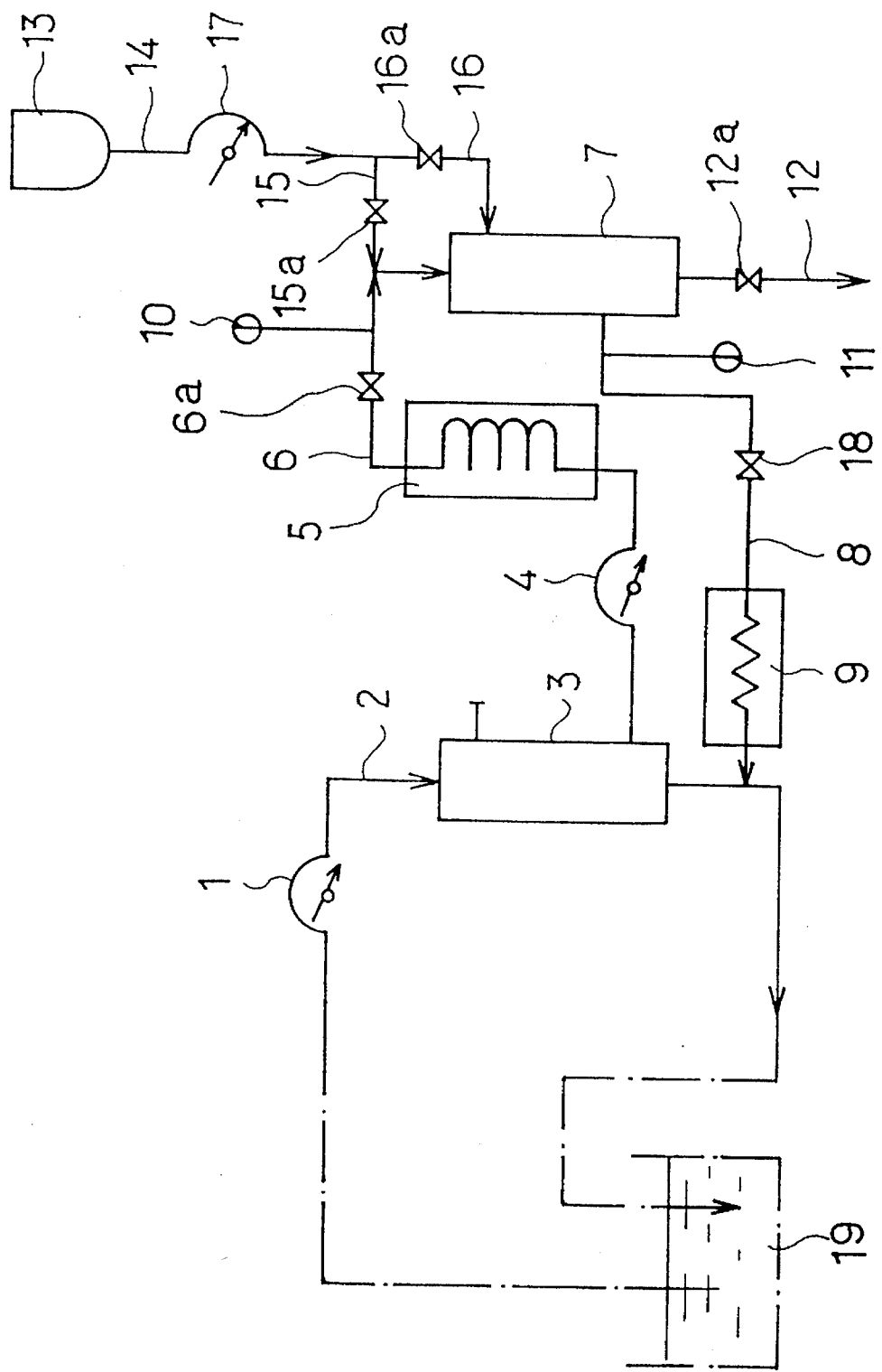
FIG. 1 is a flow chart of an apparatus suitable for practicing the method of the present invention.

An embodiment of the present invention will be described below with reference to the accompanying drawings.

FIG. 1 shows a plasma cryofiltration apparatus having a system for washing a secondary filter using the method of the present invention.

The cryofiltration apparatus has a blood pump 1, which operates to send blood from a blood supply source (blood pool 19) to a primary filter 3 through a blood line 2 to separate the blood into blood cells and plasma. By the operation of a plasma pump 4, the separated plasma is sent through a plasma line 6 provided with a cooling unit 5 to a secondary filter 7, whereby a cryogel of macromolecules formed by cooling is separated from the plasma and removed. The plasma separated from the cryogel and thereby purified is passed from the secondary filter 7 through a return line 8, heated by a warmer 9 and returned to the blood supply source (blood pool 19) while being mixed again with the blood cells returned from the primary filter 3. This cycle of cryofiltration is thereafter repeated.

When the cryofiltration apparatus of the above construction is operated for continued plasma filtration, the secondary filter tends to be gradually clogged, and there arises a need to restore the function by eliminating the clogging.

The cryofiltration apparatus shown in FIG. 1 has a washing system for restoring the function of the secondary filter 7 by practicing the washing method of the present invention.

The cleaning system comprises as a component thereof sensor means for detecting the filtration pressure within the secondary filter 7. The sensor means includes an inlet-side pressure gauge 10 and an outlet-side pressure gauge 11 provided on the plasma line 6 and the return line 8, respectively, and is adapted to produce a detection signal upon the difference between the values of these gauges 10, 11 reaching a predetermined set value.

The system further comprises as another component a waste line 12 connected to an inner chamber of the secondary filter 7. Mounted on the line 12 is a valve 12a which is, for example, of the electromagnetically operable type and which opens from a closed state in response to the detection signal from the pressure sensor means.

The system further comprises as another component means for supplying a wash liquor to the secondary filter 7. The supplying means comprises a wash liquor tank 13, and a wash liquor pump 17 for supplying the wash liquor in the tank 13 from a common line 14 to the inner and outer chambers of the secondary filter 7 individually through branch lines 15, 16. Mounted on the respective branch lines 15, 16 are valves 15a, 16a which are, for example, of the electromagnetically operable type and which open from a closed state simultaneously or with a predetermined time lag when the valve 12a on the waste line 12 is opened.

The system further comprises as the last component a valve 18, for example, of the electromagnetically operable type mounted on the return line 8. The valve 18 opens and closes in reverse relation with the valve 12a on the waste line 12.

With the washing system of the foregoing construction, the sensor means including the pressure gauges 10, 11 outputs a detection signal upon the filtration pressure in the secondary filter 7 reaching the predetermined set value, whereby the plasma pump 4 is brought out of operation, and the valve 12a on the waste line 12 is opened from the closed state at the same time. Consequently, the internal pressure of the inner chamber of the secondary filter 7 drops to atmospheric pressure, while the valve 18 on the return line 8 is closed from the open state to stop the return of the purified plasma. The valves 15a, 16a on the branch lines 15, 16 of the wash liquor supplying means are further opened from the closed state, and the wash liquor pump 17 is initiated into operation to supply the wash liquor from the tank 13 to the secondary filter 7 through the common line 14 and then through the branch lines 15, 16 and wash the filter 7 from both the inner and outer chamber sides. The amount of wash liquor is measured from the supply time or by a flowmeter (not shown). When a predetermined amount is reached, a timer (not shown) or the like outputs a signal, in response to which the wash liquor pump 17 stops its operation, and the valves 15a, 16a on the branch lines 15, 16 and the valve 12a on the waste line 12 close at the same time to complete the washing operation. On the other hand, the plasma pump 4 starts its operation, and the valve 18 on the return line 8 opens to resume the usual operation. The washing operation described is repeated every time the filtration pressure in the secondary filter 7 has reached the set value.

With the washing method of the present invention, the washing operation is started upon the filtration pressure in the secondary filter 7 (withstanding pressure 500 mmHg) reaching 350 to 500 mmHg, preferably 400 to 450 mmHg, which is considerably higher than 300 mmHg of the known washing method. The amount of wash liquor to be used for washing is 5 to 50% (18 to 180 ml), preferably 5 to 15% (18 to 54 ml) of the priming volume (e.g., 360 ml) of the secondary filter 7, and is much smaller than in the known washing method.

The washing method of the present invention is considerably higher than the conventional method in the filtration pressure at which washing is to be started, and is much less than the conventional method in the amount of wash liquor to be used, so that the reduction in the filtration efficiency after washing is much smaller than in the conventional method. The method of the invention therefore makes it possible to carry out the entire operation of plasma filtration efficiently in a range of relatively high filtration pressures despite the washing of the secondary filter and to reduce the amount of plasma to be circulated for treatment as required for the purification of plasma to a predetermined degree.

Further because the amount of liquor to be used for washing the secondary filter 7 is small, the time taken for washing can be shortened. The washing is done usually at a flow rate of about 100 ml/min and requires 20 to 108 seconds (18 to 180 ml), or 20 to 30 seconds (18 to 54 ml) in the preferred mode, each time. Filtration of 2 to 4 liters of plasma requires washing about 6 times. Accordingly, the overall washing operation takes about 120 to 648 seconds, or about 120 to 180 seconds in the preferred mode. The conventional method uses a large amount of wash liquor and therefore involves washing about 3 times, but requires an exceedingly longer period of time for washing. The flow rate of wash liquor, which is usually about 100 ml/min as stated above, is suitably variable within the range of 30 ml/min to 200 ml/min, for example, in accordance with the amount of wash liquor to be used each time or the degree of clogging.

The washing method of the present invention makes it possible to carry out the entire operation of plasma filtration efficiently with a decreased amount of plasma circulated for treatment and also with a reduction in the total time required for washing, consequently shortening the time required for the filtration of plasma.

During washing, the plasma is discharged from the secondary filter to the outside via the waste line 12 in an amount corresponding to the amount of wash liquor, whereas the amount of plasma to be discharged from the system can be diminished since a small amount of wash liquor is used according to the invention.

The filtration pressure for starting washing is preferably as high as possible in the present invention in view of the filtration efficiency, but an excessively high pressure is likely to impair the performance of the secondary filter 7 itself. Accordingly, the filtration pressure needs to be 70 to 100% of the withstanding pressure, for example, in the range of 350 to 500 mmHg when the withstanding pressure is 500 mmHg. The amount of wash liquor needs to be in the range of 5 to 50% of the priming volume of the secondary filter since the liquor markedly reduces the filtration efficiency if used in an excessive amount or fails to thoroughly refresh the filter by washing if used in too small an amount.

An example of the invention and a comparative example are given below. For comparison, the results achieved are listed in Table 1.

Invention

A blood pool 19 was installed and connected to the apparatus of FIG. 1 as indicated in phantom lines. Used as the primary filter 3 was one made of a membrane of polyethylene hollow fibers having a maximum pore size of $0.3\mu$, inside diameter of $350\mu$, membrane thickness of $50\mu$ and membrane area of $0.5$ m$^2$. Used as the secondary filter 7 was one made of a membrane of cellulose diacetate hollow fibers having a maximum pore size of $0.2\mu$, inside diameter of $370\mu$, membrane thickness of $160\mu$ and membrane area of $0.65$ m. The filter 7 was 500 mmHg in withstanding pressure and 360 ml in priming volume. Two liters of human plasma was used in place of blood. The blood pump 1 was set at a flow rate of 100 ml/min, and the plasma pump 4 at a flow rate of 30 ml/min.

The washing system was so set as to be initiated into operation upon the difference between the values of the pressure gauges 10 and 11 reaching 400 mmHg. The amount of wash liquor used was 50 ml per washing cycle. The wash liquor pump 17 was set to a flow rate of 100 ml/min.

The secondary filter 7 clogged 6 times by the time 2.75 liters of plasma was treated, and was washed every time upon clogging. FIG. 2 shows the relationship of the filtration efficiency with the frequency of washing and experimental time. The plasma protein removal ratio of the plasma pool 19 was calculated from the following equation with the result given in Table 1.

$$\text{Removal ratio (\%)} = \frac{A - B}{A} \times 100$$

wherein A is the amount of a plasma protein before filtration, and B is the amount of the plasma protein after filtration.

Comparative Example

An experiment was conducted using the same plasma and the same circuit and filters as in the case of the invention.

The washing system was so set as to be initiated into operation upon the difference between the values of the pressure gauges 10 and 11 reaching 300 mmHg.

For washing to collect albumin in particular from among the plasma proteins remaining in the secondary filter, the plasma in the secondary filter 7 was returned first to the plasma pool 19 with about 200 ml of wash liquor by stopping the plasma pump 4, closing the valve 6a, opening the valve 15a and operating the wash liquor pump 17 at a flow rate of 30 ml/min, and the secondary filter 7 was subsequently washed with about 300 ml of wash liquor by closing the valves 15a, 18, opening the valves 12a, 16a and operating the wash liquor pump 17 at a flow rate of 100 ml/min.

The secondary filter 7 clogged 3 times by the time 4 liters of plasma was treated, and was washed every time upon clogging.

The time taken for this experiment was about 170 minutes, and the wash liquor used was 1500 ml in total. FIG. 3 shows the relationship of the filtration efficiency with the frequency of washing and experimental time. The plasma protein removal ratio of the plasma pool 19 was calculated in the same manner as in the case of the invention with the result given in Table 1.

TABLE 1

|  | Example (n = 3) | Comp. Ex. (n = 3) |
|---|---|---|
| Albumin removal ratio (%) | 51.74 ± 2.83 | 53.44 ± 4.60 |
| Fibrinogen removal ratio (%) | 72.19 ± 3.38 | 71.52 ± 0.75 |
| Experimental time | 99.41 ± 1.00 | 169.52 ± 1.25 |

As will be apparent from Table 1, the present invention shortens the time required for the experiment, which is about 170 minutes in Comparative Example, to about 100 minutes while achieving plasma protein removal ratios which are comparable to those of Comparative Example.

The washing method of the present invention reduces the time required for the filtration of plasma to about 60 to 70% of the time conventionally taken to shorten the patient restraining time. Furthermore, the amount of wash liquor is much smaller than in the conventional method, leading to a diminished disposal loss of plasma from the system.

We claim:

1. In a plasma filtration process including a treatment of blood with a primary filter for separating the blood into blood cells and plasma and a treatment of the separated plasma with a secondary filter having an inner chamber and an outer chamber so as to remove harmful macromolecules from the separated plasma for purification where the secondary filter is intermittently washed with a wash liquor, a method of washing the secondary filter comprising the step of passing a wash liquor through at least one of the inner chamber and the outer chamber of the secondary filter in an amount corresponding to 5 to 50% of a priming volume of the secondary filter every time filtration pressure reaches at least 350 to 500 mm Hg wherein a withstanding pressure for the secondary filter is at least 500 mm Hg.

2. A washing method as defined in claim 1 wherein the secondary filter is 500 mmHg in withstanding pressure and is washed every time the filtration pressure has reached 400 to 450 mmHg using the liquor in an amount corresponding to 5 to 15% of the priming volume of the filter.

3. A washing method as defined in claim 1 wherein the secondary filter is 500 mmHg in withstanding pressure and 150 to 400 ml in priming volume.

4. A washing method as defined in claim 1 wherein the wash liquor is passed at a flow rate of 30 ml/min to 200 ml/min.

5. A washing method as defined in claim 1 wherein the wash liquor is passed at a flow rate of 100 ml/min.

6. A washing method as defined in claim 1 wherein the secondary filter comprises hollow fibers having a pore size of 0.01 μm to 0.1 μm.

7. A washing method as defined in any one of claims 1 to 6 wherein said plasma filtration process utilizes cryofiltration of plasma.

* * * * *

UNITED STATES PATENT AND TRADEMARK OFFICE
CERTIFICATE OF CORRECTION

PATENT NO.  : 5,516,431
DATED       : May 14, 1996
INVENTOR(S) : KAWAMURA et al.

It is certified that error appears in the above-identified patent and that said Letters Patent is hereby corrected as shown below:

On the title page:

Item [87], "PCT Pub. Date: Aug. 4, 1905" should read --PCT Pub. Date: Aug. 4, 1994--.

Signed and Sealed this

Fifteenth Day of October, 1996

Attest:

BRUCE LEHMAN

*Attesting Officer*   *Commissioner of Patents and Trademarks*